United States Patent [19]
DeCoster et al.

[11] Patent Number: 5,929,277
[45] Date of Patent: Jul. 27, 1999

[54] METHODS OF REMOVING ACETIC ACID FROM CYCLOHEXANE IN THE PRODUCTION OF ADIPIC ACID

[75] Inventors: David C. DeCoster, Buckley, Wash.; Eustathios Vassiliou, Newark, Del.; Mark W. Dassel, Indianola; Ader M. Rostami, Bainbridge Island, both of Wash.

[73] Assignee: Twenty-First Century Research Corporation, Newark, Del.

[21] Appl. No.: 08/934,253

[22] Filed: Sep. 19, 1997

[51] Int. Cl.[6] .............................. C07C 51/42; C07C 55/14
[52] U.S. Cl. .......................... 562/593; 562/590; 562/608
[58] Field of Search ..................................... 562/590, 593, 562/608

[56] References Cited

U.S. PATENT DOCUMENTS

| | | |
|---|---|---|
| 1,121,532 | 12/1914 | Newberry . |
| 2,014,044 | 9/1935 | Haswell ........................ 75/17 |
| 2,223,493 | 12/1940 | Loder ........................ 260/537 |
| 2,223,494 | 12/1940 | Loder ........................ 260/586 |
| 2,301,240 | 11/1942 | Baumann et al. .............. 183/115 |
| 2,439,513 | 4/1948 | Hamblet et al. ............... 260/533 |
| 2,557,282 | 6/1951 | Hamblet et al. ............... 260/533 |
| 2,565,087 | 8/1951 | Porter et al. .................. 260/631 |
| 2,980,523 | 4/1961 | Dille et al. ................... 48/215 |
| 3,161,603 | 12/1964 | Leyshon et al. ............... 252/413 |
| 3,231,608 | 1/1966 | Kollar ........................ 260/533 |
| 3,234,271 | 2/1966 | Barker et al. ................. 260/531 |
| 3,290,369 | 12/1966 | Bonfield et al. ............... 260/537 |
| 3,361,806 | 1/1968 | Lidov ........................ 260/531 |
| 3,515,751 | 6/1970 | Oberster et al. ............... 260/533 |
| 3,530,185 | 9/1970 | Pugi ........................ 260/586 |
| 3,613,333 | 10/1971 | Gardenier ..................... 55/89 |
| 3,677,696 | 7/1972 | Bryk et al. .................... 23/2 |
| 3,839,435 | 10/1974 | Shigeyasu et al. ............. 260/524 R |
| 3,928,005 | 12/1975 | Laslo ........................ 55/73 |
| 3,932,513 | 1/1976 | Russell ....................... 260/586 |
| 3,946,076 | 3/1976 | Paasen et al. ................. 260/586 |
| 3,957,876 | 5/1976 | Rapoport et al. .............. 260/586 |
| 3,987,100 | 10/1976 | Barnette et al. ............... 260/586 |
| 3,987,808 | 10/1976 | Carbonell et al. ............. 137/3 |
| 4,025,498 | 5/1977 | Buss et al. ................... 260/95 A |
| 4,039,304 | 8/1977 | Bechthold et al. .............. 55/10 |
| 4,055,600 | 10/1977 | Langley et al. ............... 260/586 |
| 4,065,527 | 12/1977 | Graber ....................... 261/79 A |
| 4,308,037 | 12/1981 | Meissner et al. ............... 55/10 |
| 4,332,590 | 6/1982 | Smith ........................ 23/230 A |
| 4,361,965 | 12/1982 | Goumondy et al. .............. 34/57 |
| 4,370,304 | 1/1983 | Hendriks et al. ............... 422/224 |
| 4,394,139 | 7/1983 | Board ........................ 55/20 |
| 4,419,184 | 12/1983 | Backlund ..................... 162/49 |
| 4,423,018 | 12/1983 | Lester, Jr. et al. ............ 423/243 |
| 5,061,453 | 10/1991 | Krippl et al. ................. 422/106 |
| 5,104,492 | 4/1992 | King et al. ................... 203/15 |
| 5,123,936 | 6/1992 | Stone et al. .................. 55/8 |
| 5,170,727 | 12/1992 | Nielsen ...................... 110/346 |
| 5,221,800 | 6/1993 | Park et al. ................... 562/543 |
| 5,244,603 | 9/1993 | Davis ........................ 261/87 |
| 5,270,019 | 12/1993 | Melton et al. ................ 422/234 |
| 5,271,904 | 12/1993 | Esposito et al. ............... 422/105 |
| 5,286,458 | 2/1994 | Yang et al. .................. 422/168 |
| 5,294,378 | 3/1994 | Succi et al. .................. 261/130 |

(List continued on next page.)

FOREIGN PATENT DOCUMENTS

| | | |
|---|---|---|
| 439 007 A2 | 7/1991 | European Pat. Off. . |
| 729 084 A1 | 8/1996 | European Pat. Off. . |
| 729 085 A1 | 8/1996 | European Pat. Off. . |
| 751 105 A2 | 1/1997 | European Pat. Off. . |
| 2 722 783 A1 | 1/1996 | France . |
| 4426132A1 | 1/1996 | Germany . |
| 4427474 | 2/1996 | Germany . |
| 48-003815 | 2/1973 | Japan . |
| 415 172 | 8/1934 | United Kingdom . |
| 738808 | 10/1955 | United Kingdom . |
| 864106 | 3/1961 | United Kingdom . |
| 1143213 | 2/1969 | United Kingdom ............ 51/16 |
| 2014473 | 8/1979 | United Kingdom . |
| WO96/03365 | 2/1996 | WIPO . |
| WO 96/40610 | 12/1996 | WIPO . |

OTHER PUBLICATIONS

Lewis, Hawley's Condensed Chemical Dictionary, 12th edition, pp. 7, 336, and 1076, 1993.

E. Sorribes et al., "Formación de neuvas fases en el proceso de obtención de ácido adípico: causas y efectos que provocan," Rev. R. Acad. Cienc. Exactas, Fis. Nat. Madrid (1987), 81 (1), 233–5 (+English language translation).

U.S. application No. 08/587,967, Dassel et al., filed Jan. 17, 1996.

U.S. application No. 08/812,847, Dassel et al., filed Mar. 6, 1997.

U.S. application No. 08/859,985, Vassiliou et al., filed May 21, 1997.

U.S. application No. 08/861,281, Dassel et al., filed May 21, 1997.

U.S. application No. 08/861,180, DeCoster et al., filed May 21, 1997.

U.S. application No. 08/861,176, Dassel et al., filed May 21, 1997.

U.S. application No. 08/859890, Rostami et al., filed May 21, 1997.

U.S. application No. 08/861,210, Vassiliou et al., filed May 21, 1997.

U.S. application No. 08/824,992, Dassel et al., filed Mar. 27, 1997.

U.S. application No. 08/477,195, Dassel et al., filed Jun. 7, 1995.

*Primary Examiner*—Samuel Barts
*Assistant Examiner*—Rosalynd Keys
*Attorney, Agent, or Firm*—Seed and Berry LLP

[57] ABSTRACT

This invention relates to methods of removing acetic acid from cyclohexane in the direct oxidation of cyclohexane to adipic acid, especially after recycling catalyst which is precipitated by introduction of additional cyclohexane. The removal of acetic acid is preferably conducted by use of rather small amounts of wash-water in one to three stage extractors. A two stage reactor is preferable as being more efficient.

19 Claims, 3 Drawing Sheets

U.S. PATENT DOCUMENTS

| | | | |
|---|---|---|---|
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,505,920 | 4/1996 | Kollar et al. | 423/246 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |

METHODS OF REMOVING ACETIC ACID FROM CYCLOHEXANE IN THE PRODUCTION OF ADIPIC ACID

TECHNICAL FIELD

This invention relates to methods of removing acetic acid from cyclohexane in the direct oxidation of cyclohexane to adipic acid, especially after recycling catalyst which is precipitated by introduction of additional cyclohexane.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is important to note that most studies on the Direct Oxidation have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and other intermediate oxidation products.

U.S. Pat. No. 5,463,119 (Kollar) discloses a process for the oxidative preparation of $C_5$–$C_8$ aliphatic dibasic acids by
(1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by
(1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the $C_5$–$C_8$ aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, control of oxidation reactions by adjusting the water level subject to the intricate and critical controls and requirements of the instant invention as described and claimed.

Our U.S. Pat. Nos. 5,580,531, 5,558,842, 5,502,245, 5,801,282; 5,883,292; and 5,654,475, all of which are incorporated herein by reference, describe methods and apparatuses relative to controlling reactions in atomized liquids. Our copending application Ser. No. 08/812,847, filed on Mar. 6, 1997, and our copending application Ser. No. 08/824,992, filed on Mar. 27, 1997 are both also incorporated herein by reference.

All of the following patent applications, which were filed simultaneously on May 21, 1997, are also incorporated herein by reference:

U.S. Pat. No. 5,801,273 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments";

U.S. patent application Ser. No. 08/861,281 now abandoned of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

U.S. patent application Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator";

U.S. Pat. No. 5,824,819 of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator";

U.S. Pat. No. 5,817,868 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements"; and U.S. patent application Ser. No. 08/861,210 of Eustathios Vassiliou, Ader M. Rostami, David C. DeCoster, and Mark W. Dassel, titled "Pseudo-Plug-Flow Reactor."

Further, our U.S. patent application Ser. No. 08/876,692 filed on Jun. 16, 1997, of Ader M. Rostami, David C. DeCoster, Eustathios Vassiliou, Mark W. Dassel, and Sharon M. Aldrich, titled "Methods and Devices for Controlling Hydrocarbon Oxidations to Respective Acids by Adjusting the Water Level during the Reaction" is also incorporated herein by reference.

Our PCT Patent Application No. PCT/US97/10830, filed on Jun. 23, 1997, of Mark W. Dassel, David C. DeCoster, Ader M. Rostami, Eustathios Vassiliou, and Sharon M. Aldrich, titled "Methods and Devices for Oxidizing a Hydrocarbon to Form an Acid" is incorporated herein by reference.

Also, our PCT Patent Application No. PCT/US97/12944, filed on Jul. 23, 1997, of David C. DeCoster, Eustathios Vassiliou, Mark W. Dassel, Sharon M. Aldrich, and Ader M. Rostami, titled "Methods and Devices for Controlling the Reaction Rate and/or Reactivity of Hydrocarbon to an Intermediate Oxidation Product by Adjusting the Oxidant Consumption Rate" is also incorporated herein by reference.

In addition, our U.S. patent application Ser. No. 08/900, 323 having a Docket Number 900105.414, filed on Jun. 25, 1997, of Eustathios Vassiliou, Mark W. Dassel, Sharon M. Aldrich, Ader M. Rostami, and David C. DeCoster, titled "Methods and Devices for Controlling Hydrocarbon Oxidations to Respective Acids by Adjusting the Solvent to Hydrocarbon Ratio" is also incorporated herein by reference.

Our U.S. patent application Ser. No. 08/931,035 having a Docket Number 900105.415, filed on Sep. 16, 1997, of Mark W. Dassel, Ader M. Rostami, David C. DeCoster, and Eustathios Vassiliou titled "Methods and Reactor Devices for Removing Catalyst after Oxidation of Hydrocarbons" is also incorporated herein by reference.

Further, our U.S. patent application Ser. No. 08/932,875 having a Docket Number 900105.416, filed on Sep. 18, 1997, of Ader M. Rostami, David C. DeCoster, Eustathios Vassiliou, and Mark W. Dassel, titled "Methods Of Recycling Catalyst In Oxidations Of Hydrocarbons" is also incorporated herein by reference.

SUMMARY OF THE INVENTION

As aforementioned, this invention relates to methods and devices for removing acetic acid from cyclohexane in the direct oxidation of cyclohexane to adipic acid, especially after recycling catalyst which is precipitated by introduction of additional cyclohexane. More particularly it pertains a method of separating a majority of acetic acid from a first mixture comprising cyclohexane and acetic acid, the method being characterized by a step of mixing the first mixture with an adequate amount of wash-water to form a polar phase containing the majority of the acetic acid and a non-polar phase containing a majority of the cyclohexane.

The majority of the acetic acid in the polar phase is preferably higher than 80% by weight of the acetic acid present in both phases. Also, the acetic acid in the first mixture is less than 50% by weight of the weight sum of acetic acid and cyclohexane. The amount of wash-water is preferably less than 15 parts per 100 parts of the first mixture, by weight.

Preferably, the step of mixing the first mixture with wash-water to form the polar and the non-polar phases is conducted by a two-stage counter-current extraction, and also preferably, the first mixture is produced by steps of:

(a) oxidizing cyclohexane to adipic acid with oxygen in the presence of a catalyst;

(b) at least partially removing the adipic acid;

(c) at least partially precipitating the catalyst by addition of cyclohexane; and (d) removing the precipitated catalyst.

The method may further comprise a step of reacting the adipic acid with a reactant selected from a group consisting of a polyol, a polyamine, and a polyamide in a manner to form a polymer of a polyester, or a polyamide, or a (polyimide and/or polyamideimide), respectively. The polymer may undergo spinning to form fibers.

The instant invention also relates to a device for removing at least partially (a) catalyst by adding cyclohexane to a mixture containing acetic acid and catalyst, the addition of cyclohexane causing formation of a catalyst precipitate and a mixture comprising cyclohexane and acetic acid, and (b) acetic acid from the mixture comprising cyclohexane and acetic acid, the device comprising:

a catalyst precipitation chamber;

cyclohexane addition means connected to the catalyst precipitation chamber for adding cyclohexane to the catalyst precipitation chamber and causing catalyst precipitation and formation of the mixture comprising cyclohexane and acetic acid;

catalyst removal means for removing the precipitated catalyst from the mixture comprising cyclohexane and acetic acid; and acetic acid removal means for separating at least partially the acetic acid from the mixture comprising cyclohexane and acetic acid.

The acetic acid removal means may comprise an extractor using wash-water as the extraction medium.

The wash-water extractor may be a single stage, a two-stage, or a multi-stage counter-flow extractor.

The device may further comprise water removing means for separating at least partially the water from the acetic acid.

DETAILED DESCRIPTION OF THE INVENTION

As aforementioned, this invention relates to methods and devices for removing acetic acid from cyclohexane in the direct oxidation of cyclohexane to adipic acid, especially after recycling catalyst which is precipitated by introduction of additional cyclohexane.

Figure 1:
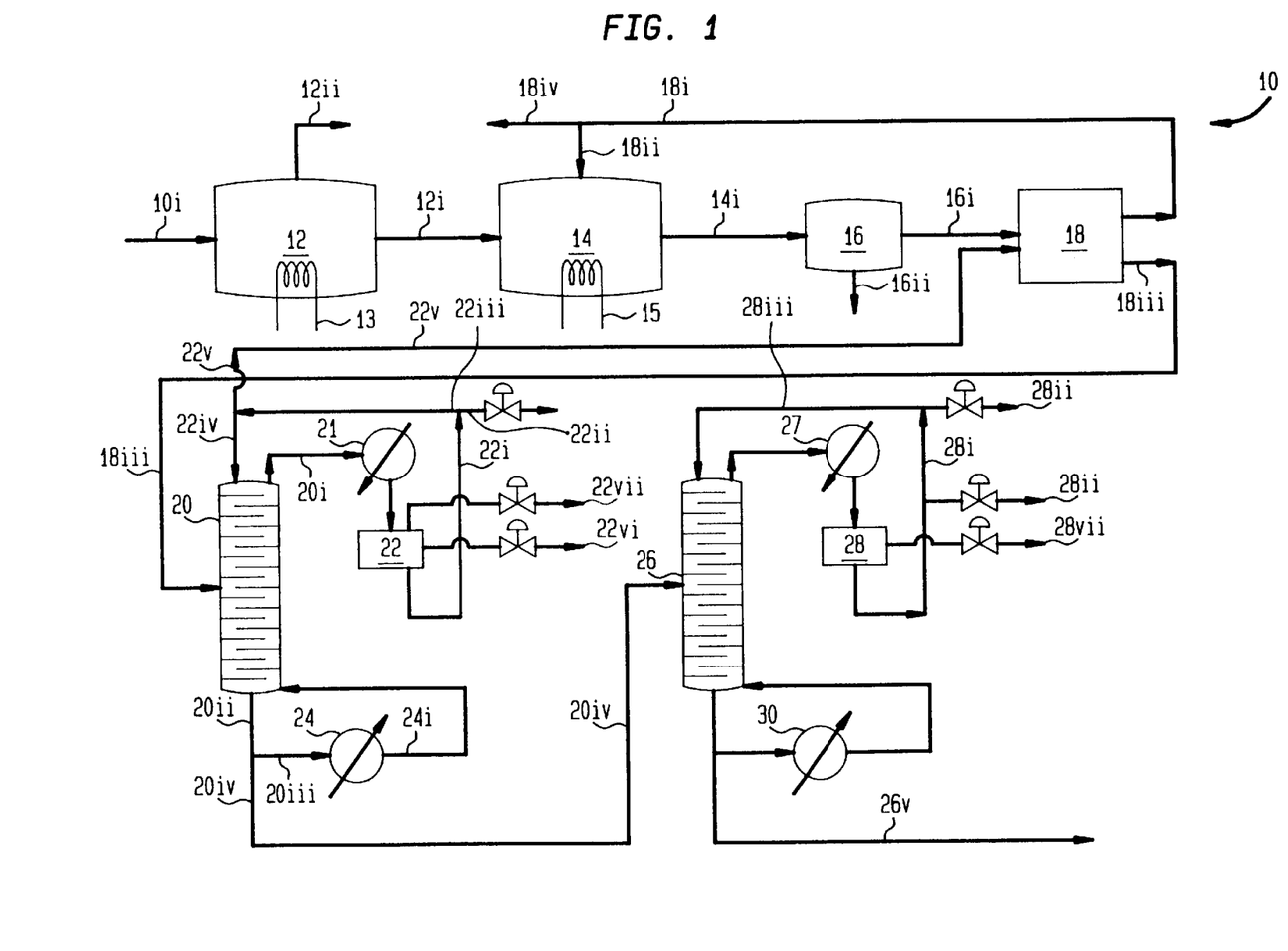
FIG. 1 is a block diagram illustrating a preferred embodiment of the present invention.

Referring now to FIG. 1, there is depicted a block diagram of a portion 10 of a reactor system for manufacturing adipic acid. This invention is concerned with any adipic acid manufacturing reactor system, by introducing the novel arrangement 10. The portion 10 of the reactor system comprises a concentration chamber 12, connected to a catalyst precipitation chamber 14, which in turn is connected to a separation chamber 16. The concentration chamber 12 is heated by any conventional type of heating means, represented by heater 13. The separation chamber 16 is connected to an extractor 18. Preferred types of extractor 18 are shown in more detail in FIGS. 2–4. The extractor 18 also communicates with the precipitation chamber 14 and with a first distillation column 20, which is serviced by a first condenser 21 connected to a decanter 22, and a first re-boiler 24. The first distillation column 20 is connected to a second distillation column 26, which is serviced by a second condenser 27 connected to a decanter 28 (vented through line 28vii), and a second re-boiler 30. The miscellaneous inlet and outlet streams connecting the different chamber will be discussed in detail in the operation of this embodiment.

In operation of this embodiment, a reaction mixture comprising cyclohexane, catalyst, acetic acid and other adjuncts, such as water, glutaric acid, succinic acid, cyclohexanol, cyclohexanol, esters, etc., enters the concentration chamber 12 through inlet line 10i. The cyclohexane in this example is unreacted cyclohexane from the formation of adipic acid. The acetic acid is a very common solvent used in the direct synthesis of adipic acid, and the catalyst in most occasions is a cobalt salt, preferably cobalt acetate tetrahydrate, which are added to the front end (not shown, but very well known to the art) of the reactor system. Preferably, the total reactor system and the portion 10 shown in FIG. 1 operate in a continuous mode.

Preferably, the major portion of the adipic acid has been removed before the reaction mixture enters the concentration chamber 12 by techniques well known to the art, such as crystallization and filtration or centrifugation, for example. The reaction mixture is heated in the concentration chamber, by means of the heater 13 to a preferable temperature in the range of 40° to 70° C., preferably under reduced pressure, such as sub-atmospheric pressure for example, through line 12ii, which line may also be connected to a vacuum source and/or to a distillation column, similar to columns 20 and 26, for example. The reaction mixture is thus concentrated in the concentration chamber 12 by evaporation of cyclohexane, water, acetic acid, and other volatiles through line 12ii. The degree of concentration is adequate for precipitation to occur in the following step.

The concentrated reaction mixture is being transferred, through line 12i, from the concentration chamber 12 to the catalyst precipitation chamber 14, where cyclohexane is added, and the mixture is maintained at a preferable temperature in the range of 60° to 110° C. by heating means represented by heater 15. The amount of cyclohexane is adequately high so that most of the catalyst, preferably over 90%, precipitates. The added cyclohexane may preferably be pre-heated, and it may be either fresh cyclohexane, or recycled cyclohexane from the extractor 18, or from any other source.

The slurry containing the precipitated catalyst is being transferred, through line 14i, to the separation chamber 16, where the precipitated catalyst is separated, preferably by filtration and/or centrifugation, and leaves the chamber 16 through line 16ii for recycling to the reaction chamber (not shown), preferably without further treatment. The filtrate/centrifugate or first mixture is being transferred to the extractor 18, where a small amount of water extracts the major amount of the acetic acid, and other adjuncts, such as dibasic acids, for example along with a very small amount of cyclohexane. The water needed for the extraction may be fresh water, or it may be recycled water from the first distillation column 20, and provided to the extractor 18 through line 22v, as it will be explained later in more detail.

The two streams entering the extractor from lines 16i and 22v are mixed together, and the mixture causes the formation of two phases, one polar phase at the bottom and one non-polar phase at the top. The top non-polar phase, predominantly containing cyclohexane, may be recycled from line 18i preferably partially to the catalyst precipitation chamber 14 through line 18ii, and partially to the reaction chamber (not shown) of the reactor system, through line 18iv. The polar phase containing acetic acid, water, and other adjuncts, such as dibasic acids, for example, with a very small amount of cyclohexane, is preferably directed to the distillation column 20.

In the distillation column 20, the water and the very small amount of cyclohexane are removed by techniques well known to the art. In short, the water and cyclohexane vapors pass through line 20i to the condenser 21. The condensate is directed to the decanter 22, where it separates to an upper cyclohexane phase and a lower water phase. The decanter 22 is vented through line 22vii. At least part of the condensed water passes through line 22i, 22iii, and 22iv, back to the top of the distillation column 20, and as it moves downward it condenses vapors of acetic acid, which otherwise would enter line 20i and condenser 22. Part of the condensed water is removed through line 22ii, for further treatment, use, or disposal, if so desired, and part of the condensed water is recycled to the extractor 18 through line 22v, if so desired. The cyclohexane is removed through line 22vi and it is directed (not shown) either to chamber 14, or to the reaction chamber (not shown), or it is disposed in any other desirable way.

At the bottom of the column 20, condensed acetic acid with other high boilers passes through line 20ii, and preferably, part of it enters the re-boiler 24 through line 20iii, follows line 24i, and enters the bottom of column 20. Vapors of acetic acid in the vicinity of the bottom of column 20 do not allow any water to or cyclohexane condense, and condensed acetic acid with other high boilers enter the line 20ii, as aforementioned.

Part of the acetic acid containing other adjuncts, is preferably transferred to the second distillation column 26, where it is treated in a similar manner. In column 26, the acetic acid is separated from other high boilers, including adjuncts, such as dibasic acids, for example. Part of the condensed acetic acid is removed through line 28ii, preferably for recycling to the reaction chamber (not shown), and part of it is recycled to the column 26, through lines 28i and 28iii, for purposes similar to the ones described above.

High boilers including adjuncts, such as dibasic acids, for example, are removed through line 26v, preferably for further treatment. The further treatment may involve re-crystallizations, or esterifications, etc.

A computerized simulation program, supported by experimental results, was used by the inventors to calculate the material flow rates involved in reducing the percentage of acetic acid, in a mixture of cyclohexane and acetic acid, from 20% to 2%. All percentages were calculated by weight.

Figure 2:
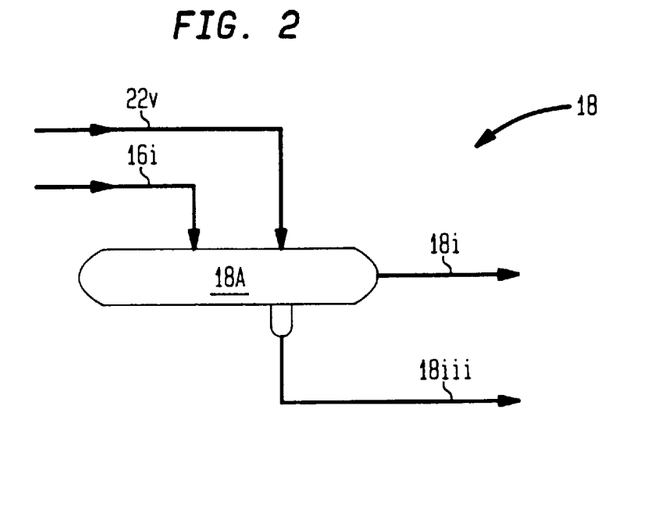
FIG. 2 is a block diagram illustrating a single-stage extractor according to the present invention.

For example, in a single-stage extractor, better shown in FIG. 2, comprising a first mixer/decanter 18A, a cyclohexane/acetic acid mixture stream containing 20% acetic acid is being fed to the mixer decanter 18A through line 16i, at a rate 100 lb. per hour, while a stream of water enters the same first mixer/decanter at a rate of 13 lb. per hour. After the two streams are mixed and decanted, a non-polar stream containing 98% cyclohexane and 2% acetic acid (with an insubstantial amount of water amounting to about 0.02%) exits the first mixer/decanter 18A through line 18*i* at a rate of about 81 lb. per hour, while a polar stream of about 41% water and 59% acetic acid (with an insubstantial amount of cyclohexane amounting to about less than 0.5%) exits the first mixer/decanter 18A through line 18*iii* at a rate of about 32 lb. per hour.

Figure 3:
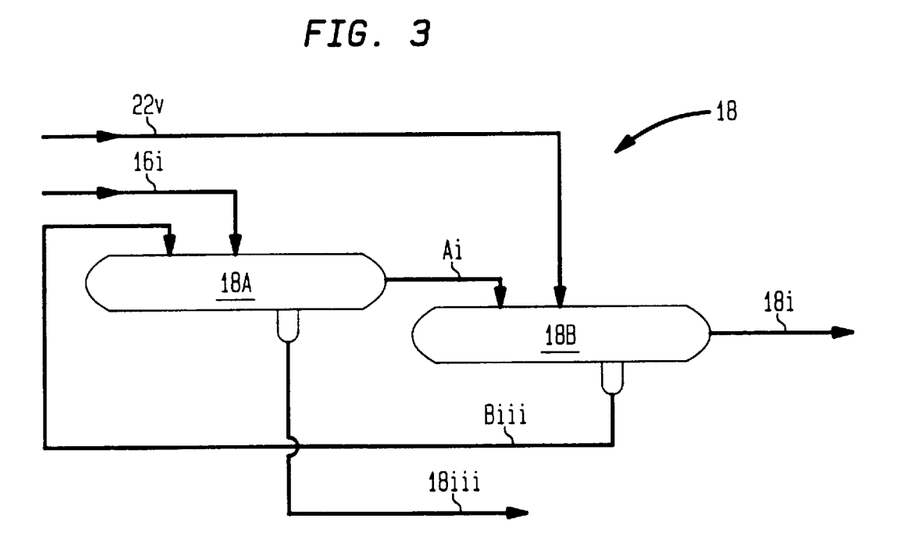
FIG. 3 is a block diagram illustrating a two-stage counter-flow extractor according to the present invention.

In another example, in a two-stage extractor, better shown in FIG. 3, comprising a first mixer/decanter 18A and a second mixer/decanter 18B, a cyclohexane/acetic acid mixture stream containing 20% acetic acid is being fed to the first mixer/decanter 18A through line 16*i*, at a rate 100 lb. per hour. A stream of water enters the second mixer/decanter 18B at a rate of 3 lb. per hour through line 22*v*. The final result is that a non-polar stream containing 98% cyclohexane and 2% acetic acid (with an insubstantial amount of water amounting to about 0.02%) exits the second mixer/decanter 18B through line 18*i* at a rate of about 81 lb. per hour, while a polar stream of about 4% cyclohexane, 14% water and 82% acetic acid exits the first mixer/decanter 18A through line 18*iii* at a rate of about 23 lb. per hour. The counter-flow arrangement in FIG. 3 is based on that the non-polar phase (about 93% cyclohexane and 7% acetic acid with an insubstantial amount of water) is transferred from the first mixer/decanter 18A to the second mixer/decanter 18B, through line Ai, at a rate of 85 lb. per hour, while the polar stream from the second mixer/decanter 18B (about 41% water and 59% acetic acid with an insubstantial amount of cyclohexane amounting to about less than 0.5%) is transferred to the first mixer/decanter 18A through line Biii at a rate of about 8 lb. per hour.

Figure 4:
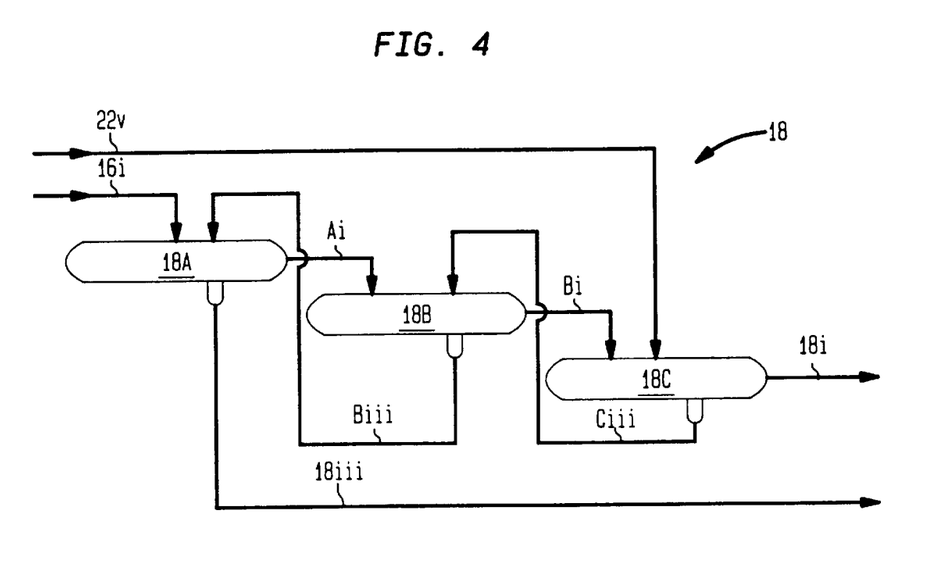
FIG. 4 is a block diagram illustrating a three-stage counter-flow extractor according to the present invention.

In another example, in a three-stage extractor, better shown in FIG. 4, comprising a first mixer/decanter 18A, a second mixer/decanter 18B, and a third mixer/decanter 18C, a cyclohexane/acetic acid mixture stream containing 20% acetic acid is being fed to the first mixer/decanter 18A through line 16*i*, at a rate 100 lb. per hour. A stream of water enters the third mixer/decanter 18C at a rate of 2 lb. per hour through line 22*v*. The final result is that a non-polar stream containing 98% cyclohexane and 2% acetic acid (with an insubstantial amount of water amounting to about 0.02%) exits the third mixer/decanter 18C through line 18*i* at a rate of about 80 lb. per hour, while a polar stream of about 6% cyclohexane, 19% water and 79% acetic acid exits the first mixer/decanter 18A through line 18*iii* at a rate of about 23 lb. per hour. The counter-flow arrangement in FIG. 4 is based on the following flows:

The non-polar phase (about 89% cyclohexane and 11% acetic acid with an insubstantial amount of water) is transferred from the first mixer/decanter 18A to the second mixer/decanter 18B at a rate of 89 lb. per hour, through line Ai;

the non-polar phase (about 95% cyclohexane and 5% acetic acid with an insubstantial amount of water) is transferred from the second mixer/decanter 18B to the third mixer/decanter 18C at a rate of 83 lb. per hour, through line Bi;

the polar stream from the third mixer/decanter 18C (about 40% water and 59% acetic acid with an insubstantial amount of cyclohexane amounting to about less than 1%) is transferred to the second mixer/decanter 18B at a rate of about 5 lb. per hour through line Ciii; and the polar stream from the second mixer/decanter 18B (about 19% water, 79% acetic acid and 2% cyclohexane) is transferred to the first mixer/decanter 18A at a rate of about 8 lb. per hour, through line Biii.

As aforementioned, the above results are based on computerized simulation, and therefore, they cannot be considered to be absolutely accurate. However, they show very clearly that good removal of acetic acid from a mixture of cyclohexane may be achieved with an extractor using wash-water as the medium of extraction. Although more than three-stage counter-flow extractors may be used, it is preferable that one-stage to three-stage extractors are used. It is even more preferable that a two stage counter-flow extractor is used, since there is a large difference in extraction efficiency going from one stage to two stages, the efficiency difference between the two and three stages is rather small.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example, pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be at each instance. The expert systems are programmed based on the expertise of experienced human beings. The fuzzy logic systems are based on intuition rules in addition to expertise rules.

Regarding adipic acid, the preparation of which is especially suited to the methods and apparatuses of this invention, general information may be found in a plethora of U.S. patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

We claim:

1. A method of treating a first mixture produced by oxidation of cyclohexane to adipic acid with oxygen in the presence of a catalyst and acetic acid, the method comprising the steps of:

(a) at least partially removing the adipic acid;

(b) adding cyclohexane in order to at least partially precipitate the catalyst:

(c) removing the precipitated catalyst;

(d) adding an adequate amount of wash-water to form a polar phase containing a majority of the acetic acid, and a non-polar phase containing a majority of cyclohexane; and (e) separating the polar phase containing the majority of the acetic acid from the non-polar phase.

2. A method as defined in claim 1 wherein the majority of the acetic acid in the polar phase is higher than 80% by weight of the acetic acid present in both phases.

3. A method as defined in claim 1 wherein the majority of the cyclohexane in the non-polar phase is higher than 80% by weight of the cyclohexane present in both phases.

4. A method as defined in claim 2 wherein the majority of the cyclohexane in the non-polar phase is higher than 80% by weight of the cyclohexane present in both phases.

5. A method as defined in claim 1 wherein the amount of wash-water is less than 15 parts per 100 parts of the first mixture, by weight.

6. A method as defined in claim 2 wherein the amount of wash-water is less than 15 parts per 100 parts of the first mixture, by weight.

7. A method as defined in claim 3 wherein the amount of wash-water is less than 15 parts per 100 parts of the first mixture, by weight.

8. A method as defined in claim 4 wherein the amount of wash-water is less than 15 parts per 100 parts of the first mixture, by weight.

9. A method as defined in claim 1 wherein the acetic acid in the first mixture is less than 50% by weight of the weight sum of acetic acid and cyclohexane.

10. A method as defined in claim 4 wherein the acetic acid in the first mixture is less than 50% by weight of the weight sum of acetic acid and cyclohexane.

11. A method as defined in claim 5 wherein the acetic acid in the first mixture is less than 50% by weight of the weight sum of acetic acid and cyclohexane.

12. A method as defined in claim 8 wherein the acetic acid in the first mixture is less than 50% by weight of the weight sum of acetic acid and cyclohexane.

13. A method as defined in claim 1 wherein the step of mixing the first mixture with wash-water to form the polar and the non-polar phases is conducted by a two-stage counter-current extraction.

14. A method as defined in claim 4 wherein the step of mixing the first mixture with wash-water to form the polar and the non-polar phases is conducted by a two-stage counter-current extraction.

15. A method as defined in claim 5 wherein the step of mixing the first mixture with wash-water to form the polar and the non-polar phases is conducted by a two-stage counter-current extraction.

16. A method as defined in claim 8 wherein the step of mixing the first mixture with wash-water to form the polar and the non-polar phases is conducted by a two-stage counter-current extraction.

17. A method as defined in claim 9 wherein the step of mixing the first mixture with wash-water to form the polar and the non-polar phases is conducted by a two-stage counter-current extraction.

18. A method as defined in claim 10 wherein the step of mixing the first mixture with wash-water to form the polar and the non-polar phases is conducted by a two-stage counter-current extraction.

19. A method as defined in claim 12 wherein the step of mixing the first mixture with wash-water to form the polar and the non-polar phases is conducted by a two-stage counter-current extraction.

* * * * *